United States Patent [19]

Taylor

[11] Patent Number: Plant 7,119

[45] Date of Patent: Jan. 23, 1990

[54] PLUM 'GYPSY RED'

[75] Inventor: James W. Taylor, Dinuba, Calif.

[73] Assignee: Ito Packing Co., Inc., Reedley, Calif.

[21] Appl. No.: 195,859

[22] Filed: May 19, 1988

[51] Int. Cl.[4] ..... A01H 5/00

[52] U.S. Cl. ..... Plt./38

[58] Field of Search ..... Plt./38

*Primary Examiner*—James R. Feyrer

*Attorney, Agent, or Firm*—Dennis B. Haase

[57] ABSTRACT

A new and distinct variety of plum tree of a red fleshed, cling stone fruit variety, attractive in appearance and maturing in the late season period.

1 Drawing Sheet

BACKGROUND OF THE VARIETY

The present invention relates to a new and distinct variety of plum tree, which I refer to as Gypsy Red, of a red fleshed, cling stone fruit, attractive in appearance, maturing in the late season period, which was developed from a continued fruit breeding program.

ORIGINAL AND ASEXUAL REPRODUCTION OF THE NEW VARIETY

This novel plum was derived from an ongoing fruit breeding program dedicated to the improvement of plums to enhance consumer quality and market acceptability. Propagation was effected by taking seed from the Elephant Heart variety which was stratified and grown to a height of about 18 inches. These seedlings were bud grafted into dehorned orchard trees in the experimental orchard of Ito Packing Co., Inc., Reedley, Calif., for testing and selection. Each clone was budded into several limbs to make sure that it propagated true to type.

SUMMARY OF THE VARIETY

The instant variety developed through the above method was selected because of its excellent eating quality which is somewhat better than other fine quality red fleshed plums because of its much lower acid content and high sugar content. The novel plum of the present invention is much larger than other commercial varieties and much more attractive in appearance than most other red fleshed varieties.

BRIEF DESCRIPTION OF THE DRAWING

The accompanying drawing illustrates typical specimens of the fruit and foliage of my new variety as grown in the San Joaquin Valley of California. Three specimens are shown, one of which is in the side elevation, while the other two are shown from the apex view, one with the bloom present; yet another specimen is a sectional side elevation illustrating the internal texture and color, a characteristic twig and individual leaves are shown.

DETAILED DESCRIPTION

The following is a detailed description of my new variety with color reference being to the Maerz and Paul Dictionary of Colors, except in instances where terminology having generally accepted meaning is employed.

Parentage: Open pollenated seedling of the variety Elephant Heart.

Propagation: Maintains its distinguishing characteristics through several bud grafts.

Locality where grown and observed: Near Reedley, Calif., County of Fresno, Calif.

TREE

Size: Large, upright.

Vigor: Vigorous, productive.

Regularity of bearing: Regular bearer.

Trunk: Medium size; medium texture.

Leaves:

*Color.*—Top side, 32C11; underside, 31H9.

*Size.*—Average length—2½ inches; average width of ⅞ inch; thick.

*Petiole.*—Thicker than most other varieties of the *P. salicina* species.

*Glandular characterstics.*—Wanting on many leaves but present on some. Small globose present at the base of the leaf blade or on the petiole near the leaf blade. Average gland count is three (3).

Flower bud: Medium size.

Flower: Medium size, white.

*Anthers.*—Yellow. Time of full bloom: At end of the variety Santa Rosa.

Pollination: The variety is self sterile but sets satisfactorily in mixed plantings that contain Santa Rosa and Laroda.

Productivity and thinning: This information is only available thorugh orchard experience and the variety has not gone to nursery and orchard.

FRUIT

Maturity: When described, firm ripe, Aug. 5, 1987.

Date of first picking: Aug. 5, 1987.

Date of last picking: Aug. 15, 1987.

Size: Average axial length 2½ inches; average transverse width in suture plane 2⅝ inches.

Form: Essentially round, but often slightly compressed toward the apex on the left side of the ventral suture.

*Suture.*—Smooth and very little depression.

*Ventral surface.—Round.*

*Cavity.*—Round, shallow.

*Base.*—Flatended slightly.

*Apex.*—Smooth.

*Axial diameter.*—2½ inches.

*Transverse diameter.*—2⅝ inches.

Skin:

*Thickness.*—Medium thick; medium texture.

*Tendency to crack.*—None observed.

*Bloom.*—Medium.

*Color.*—Base color where fruit is attached to the limb yellow with green tinge (20K1). Overall color redish purple (52D7), darkening to 53K4 as the fruit matures and deepening to 55L11 in the final stages of maturity. Characteristic dots occur sparsely over most of the surface.

Flesh:

*Texture.*—Firm, juicy.

*Color.*—When hard ripe, red around the pit (2L4) in general, but lighter throughout most of the flesh, however, as it matures to soft ripeness, it changes to a very dark red (55L11).

*Amygdalin.*—Slight amount present.

*Fibers.*—Few.

*Ripening.*—Evenly.

*Flavor.*—Very sweet with pleasant acid balance. Fine quality of Satsuma variety, but with less acid.

*Aroma.*—Quite pronounced.

*Juice.*—Information not available at this time.

*Eating quailty.*—Excellent.

Stone:

*Adherence to flesh.*—Generally clinging but separates easily from the fruit.

*Size.*—Average thickness, $\frac{3}{8}$ inch; average width, $\frac{3}{4}$ inch; average length, 1 inch.

*Form.*—Oval.

*Hilum.*—Very small, oval.

*Dorsal edge.*—Shallow groove, interrupted toward apex.

*Ventral edge.*—Wing continuous from near base to about $\frac{1}{4}$ inch from the apex.

*Fruit bloom.*—The fruit bloom coloration has not been defined at this time.

*Surface.*—Irregularly pitted.

*Color.*—Brown.

Use: Market, with deep red juice, distinctive for fruit mixes.

Keeping quality: Excellent. Can be harvested at hard ripe stage and will hold in storage for a long period.

Shipping quality: Excellent.

Resistance to disease: Similar to other major *P. salicina* varieties.

Although this novel variety of plum tree possesses the described characteristics as a result of the growing conditions in Fresno County, Calif., in the central portion of the San Joaquin Valley, it is to be understood that variations of the usual magnitude in characteristics incident to growing condition, fertilization, pruning and pest control are to be expected.

Having thus described and illustrated my new variety of plum tree, what is claimed as new and described to be secured by Letters Patent is:

1. A new and distinct variety of plum tree with fruit of a red fleshed cling type, substantially as herein shown and described, and having a late maturity period, making it available for the late season, with fruit having a low acid and high sugar content, the fruit being very large with a deep purplish red exterior color.

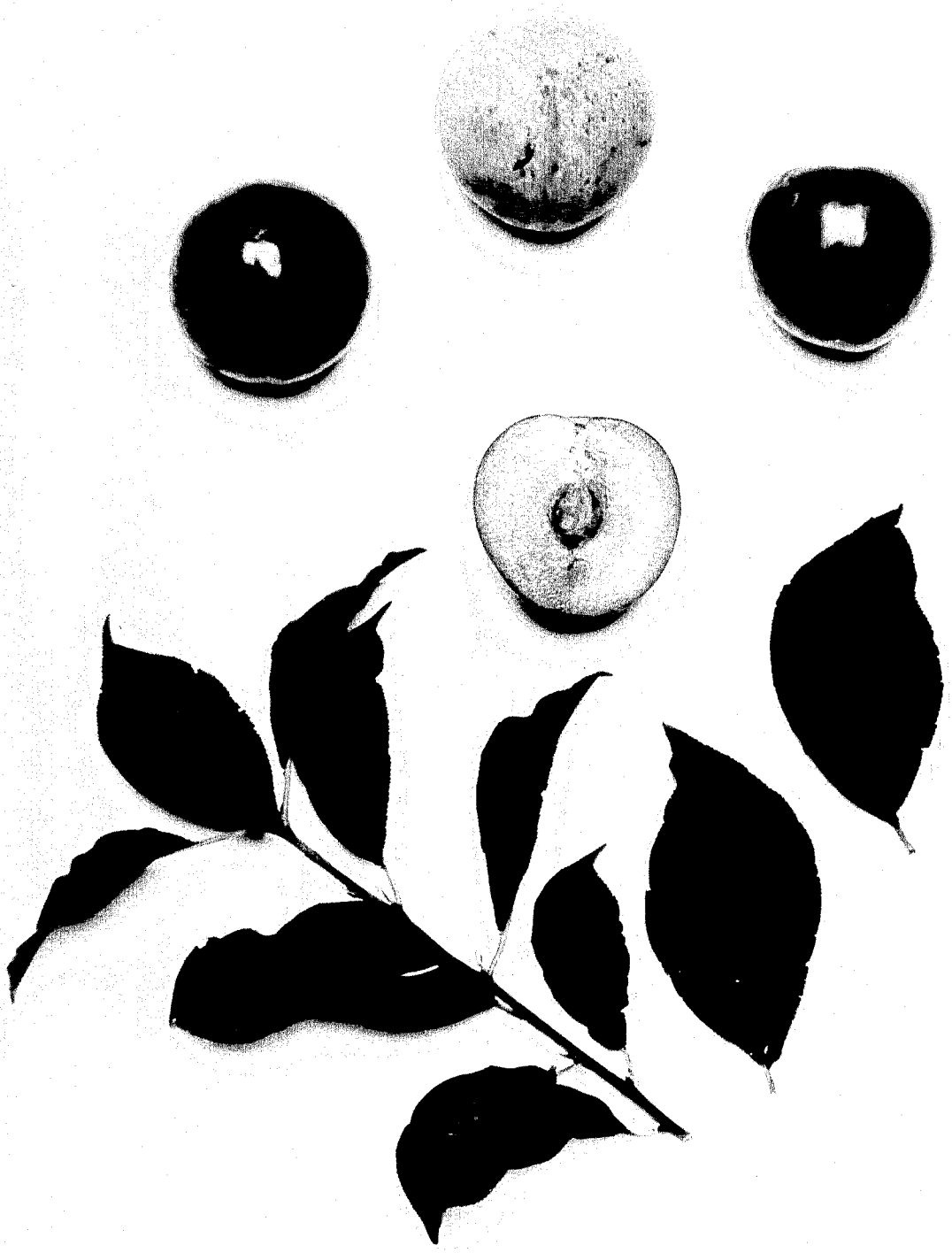

* * * * *